(12) United States Patent
Mi et al.

(10) Patent No.: US 8,506,495 B2
(45) Date of Patent: Aug. 13, 2013

(54) IMPLANTABLE MEDICAL DEVICES WITH PIEZOELECTRIC ANCHORING MEMBER

(75) Inventors: Bin Mi, Plymouth, MN (US); Lance E. Juffer, Lino Lakes, MN (US); Keith R. Maile, New Brighton, MN (US); Abhijeet V. Chavan, Maple Grove, MN (US); Thomas W. Piaget, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 457 days.

(21) Appl. No.: 12/774,983

(22) Filed: May 6, 2010

(65) Prior Publication Data

US 2010/0317929 A1    Dec. 16, 2010

Related U.S. Application Data

(60) Provisional application No. 61/185,739, filed on Jun. 10, 2009.

(51) Int. Cl.
 *A61B 5/02* (2006.01)
(52) U.S. Cl.
 USPC ............ 600/481; 600/485; 600/486; 600/504
(58) Field of Classification Search
 USPC .......................... 600/481–485, 486, 488, 561
 See application file for complete search history.

(56) References Cited

U.S. PATENT DOCUMENTS

| | | | |
|---|---|---|---|
| 5,329,200 A * | 7/1994 | Zaitsu ...................... 310/316.01 |
| 6,013,969 A * | 1/2000 | Noma et al. .................. 310/318 |
| 6,140,740 A | 10/2000 | Porat et al. |
| 6,141,588 A | 10/2000 | Cox et al. |
| 6,198,198 B1 * | 3/2001 | Fujimura et al. ......... 310/316.01 |
| 6,231,516 B1 * | 5/2001 | Keilman et al. ............... 600/485 |
| 6,764,446 B2 | 7/2004 | Wolinsky et al. |
| 6,869,404 B2 | 3/2005 | Schulhauser et al. |
| 7,024,248 B2 | 4/2006 | Penner |
| 7,081,683 B2 | 7/2006 | Ariav |
| 7,283,874 B2 | 10/2007 | Penner |
| 7,649,305 B2 | 1/2010 | Priya et al. |
| 2006/0009818 A1 * | 1/2006 | Von Arx et al. ................. 607/60 |
| 2006/0149329 A1 * | 7/2006 | Penner ........................... 607/32 |

(Continued)

OTHER PUBLICATIONS

"First Draft of Standard on Vibration Energy Harvesting", 2nd Annual Energy Harvesting Workshop, Fort Worth, TX, Jan. 30-31, 2007.

(Continued)

*Primary Examiner* — Patricia Mallari
*Assistant Examiner* — Puya Agahi
(74) *Attorney, Agent, or Firm* — Faegre Baker Daniels LLP

(57) ABSTRACT

Methods, systems, and apparatus for powering and/or recharging medical devices implanted within the body are described. An illustrative implantable medical device includes a housing having an internal cavity and a flexible anchor assembly that is coupled to the housing. The flexible anchor assembly includes a first electrical conductor, a second electrical conductor, and a piezoelectric layer that is disposed between the first and second electrical conductors and that is configured to displace in response to a physiologic force applied to the flexible anchor assembly and generate a voltage differential between the first and second electrical conductors. The implantable medical device includes power circuitry that converts the voltage differential between the first and second electrical conductors into an operating current for powering one or more components within the implantable medical device and/or for recharging a rechargeable power supply within the device.

4 Claims, 14 Drawing Sheets

(56) References Cited

U.S. PATENT DOCUMENTS

| | | | |
|---|---|---|---|
| 2006/0217776 A1* | 9/2006 | White et al. | 607/35 |
| 2007/0035202 A1* | 2/2007 | Imai | 310/311 |
| 2007/0074731 A1 | 4/2007 | Potter | |
| 2007/0252479 A1* | 11/2007 | Ishikawa | 310/339 |
| 2007/0284969 A1 | 12/2007 | Xu | |
| 2008/0004904 A1 | 1/2008 | Tran | |
| 2008/0067618 A1* | 3/2008 | Wang et al. | 257/415 |
| 2008/0103553 A1* | 5/2008 | Penner et al. | 607/60 |
| 2008/0312720 A1* | 12/2008 | Tran et al. | 607/61 |
| 2009/0025459 A1 | 1/2009 | Zhang et al. | |
| 2009/0025773 A1 | 1/2009 | Stark | |
| 2009/0160292 A1 | 6/2009 | Whinnery | |
| 2009/0171404 A1* | 7/2009 | Irani et al. | 607/2 |
| 2009/0171413 A1* | 7/2009 | Zenati et al. | 607/32 |
| 2009/0171448 A1* | 7/2009 | Eli | 623/1.32 |
| 2009/0179523 A1* | 7/2009 | Wang et al. | 310/338 |
| 2009/0216292 A1* | 8/2009 | Pless et al. | 607/33 |
| 2009/0228078 A1* | 9/2009 | Zhang et al. | 607/62 |
| 2010/0063557 A1* | 3/2010 | Imran | 607/4 |
| 2010/0076517 A1* | 3/2010 | Imran | 607/35 |
| 2010/0133954 A1* | 6/2010 | Despesse et al. | 310/319 |
| 2010/0141052 A1* | 6/2010 | Hyde et al. | 307/151 |
| 2010/0160994 A1* | 6/2010 | Feldman et al. | 607/33 |
| 2010/0171394 A1* | 7/2010 | Glenn et al. | 310/339 |
| 2010/0177488 A1* | 7/2010 | Rhodes et al. | 361/748 |
| 2010/0253184 A1* | 10/2010 | Choi et al. | 310/339 |
| 2010/0294976 A1* | 11/2010 | Ajayan et al. | 252/62.9 PZ |
| 2010/0295419 A1* | 11/2010 | Fujii | 310/339 |
| 2010/0317977 A1 | 12/2010 | Piaget et al. | |
| 2010/0317978 A1 | 12/2010 | Maile et al. | |

OTHER PUBLICATIONS

Hausler, E. et al., "Implantable Physiological power Supply With PVDF Film", Ferroelectrics, 1984, vol. 60, pp. 277-282.

Kymissis, John et al., "Parasitic Power Harvesting in Shoes", Presented at the Second IEEE International Conference on Wearable Computing, Aug. 1998, 8 pages.

Meninger, Scott et al., "Vibration-to-Electric Energy Conversion", IEEE Transactions on Very Large Scale Integration (VLSI) Systems, vol. 9, No. 1, Feb. 2001, pp. 64-76.

Mitcheson, Paul D. et al., "Architectures for Vibration-Driven Micropower Generators", Journal of Microelectromechanical Systems, vol. 13, No. 3, Jun. 2004, pp. 429-440.

Park, G. et al., "Energy Harvesting for Structural Health Monitoring Sensor Networks", Los Alamos National Laboratory, LA-14314-MS, Issued Feb. 2007.

Roundy, Shad et al., "A study of low level vibrations as a power source for wireless sensor nodes", Computer Communications 26 (2003) 1131-1144.

Roundy, Shad et al., "Improving Power Output for Vibration-Based Energy Scavangers", Pervasive Computing, Jan.-Mar. 2005, pp. 28-36.

Roundy, Shad et al., "Micro-Electrostatic Vibration-To-Electricity Converters", 2002 ASME International Mechanical Engineering Congress & Exposition, New Orleans, Louisiana 17-22, 2002.

Saez, M. Loreto Mateu, "Energy Harvesting from Passive Human Power", PhD Thesis Project, Jan. 2004.

Seiko Kinetic Direct Drive, downloaded from http://www.seikowatches.com/technology/kinetic/kinetic_dd.html, © 2007-2011, Seiko Watch Corporation.

Stark, Bernard H. et al., "Converter Circuit Design, Semiconductor Device Selection and Analysis of Parasitics for Micropower Electrostatic Generators", IEEE Transactions on Power Electronics, vol. 21, No. 1, Jan. 2006, pp. 27-37.

Wang, Zhong Lin, "Energy Harvesting for Self-Powered Nanosystems", Nano Res (2008) 1:1-8.

* cited by examiner

IMPLANTABLE MEDICAL DEVICES WITH PIEZOELECTRIC ANCHORING MEMBER

CROSS-REFERENCE TO RELATED APPLICATIONS

This application claims benefit of U.S. Provisional Application No. 61/185,739, filed on Jun. 10, 2009, entitled "Implantable Medical Devices with Piezoelectric Anchoring Member," which is incorporated herein by reference in its entirety.

TECHNICAL FIELD

The present invention relates generally to implantable medical devices including rechargeable power sources. More specifically, the present invention pertains to methods, systems, and apparatus for powering and/or recharging medical devices implanted within the body.

BACKGROUND

Actively powered implantable medical devices sometimes require a power supply such as a battery or power capacitor to provide electrical power to the device, in some cases over an extended period of time. In cardiac rhythm management applications, for example, an implantable medical device such as a pressure sensor may require a power supply capable of operating the device over a period of several years. In some cases, the time required to power the device is beyond the capability of the power supply, requiring replacement of the power supply or the implantation of a new device within the body.

With advances in power management and battery technology, more recent trends have focused on the use of small rechargeable power sources for providing power to implantable devices. Current charging techniques often rely on the patient and/or a health-care provider to ensure that the battery is charged periodically. In some cases, the patient may be required to undergo recharging using an external recharging device within a clinical environment, which can be burdensome to the patient and often adds to the overall costs associated with recharging.

SUMMARY

The present invention pertains to methods, systems, and apparatus for powering and/or recharging medical devices implanted within the body. Example 1 is an illustrative implantable medical device that includes a housing having an internal cavity and a flexible anchor assembly that is coupled to the housing. The flexible anchor assembly includes a first electrical conductor, a second electrical conductor, and a piezoelectric layer disposed between the first and second electrical conductors, the piezoelectric layer configured to displace in response to a physiologic force applied to the flexible anchor assembly and generate a voltage differential between the first and second electrical conductors. Power circuitry is configured to convert the voltage differential between the first and second electrical conductors into an operating current for powering one or more components of the implantable medical device.

In Example 2, the implantable medical device of Example 1, further including a sensor module that is disposed within the interior cavity of the housing and that is configured to sense one or more physiologic parameters within a body lumen.

In Example 3, the implantable medical device of Example 1 or Example 2 in which the flexible anchor assembly is configured to secure the implantable medical device within the body lumen.

In Example 4, the implantable medical device of Example 2 or Example 3 in which at least a portion of the flexible anchor assembly is configured to displace in response to periodic pressure pulses within the body lumen.

In Example 5, the implantable medical device of any of Examples 1 to 4 in which the flexible anchor assembly is configured to be helically wound within a blood vessel such that at least a portion of the flexible anchor assembly displaces in response to periodic vessel diameter fluctuations.

In Example 6, the implantable medical device of Example 1 in which the flexible anchor assembly further includes a tissue attachment structure disposed at an end of the flexible anchor assembly opposite an end coupled to the housing, the tissue attachment structure being configured for attachment to a structure within a patient.

In Example 7, the implantable medical device of Example 6 in which displacement of the housing in response to physiologic forces causes the piezoelectric layer to displace and generate a voltage differential between the first and second electrical conductors.

In Example 8, the implantable medical device of any of Examples 1 to 7, further including a wireless communication module disposed within the internal cavity.

In Example 9, the implantable medical device of any of Examples 1 to 8, further including a rechargeable power supply disposed within the internal cavity.

In Example 10, the implantable medical device of any of Examples 1 to 9 in which the flexible anchor assembly includes a helical structure having a helical piezoelectric ribbon having a first surface and an opposing second surface, with the first electrical conductor being disposed in contact with the first surface of the helical piezoelectric ribbon and the second electrical conductor being disposed in contact with the second surface of the helical piezoelectric ribbon.

Example 11 is an implantable sensor for sensing one or more physiologic parameters within a body lumen. The sensor includes a housing with an exterior housing wall having an inner surface and an outer surface, the exterior housing wall defining an internal cavity. A sensor module is disposed within the interior cavity of the housing and is configured to sense one or more physiologic parameters within the body lumen. A flexible anchor assembly is coupled to the housing. The flexible anchor assembly includes a first electrical conductor, a second electrical conductor, and a piezoelectric layer disposed between the first and second electrical conductors, the piezoelectric layer configured to displace in response to periodic pressure pulses within the body lumen and generate a voltage differential between the first and second electrical conductors. Power circuitry is configured to convert the voltage differential between the first and second conductors into an operating current for powering one or more components of the implantable sensor.

In Example 12, the implantable sensor of Example 11 in which the one or more components includes a rechargeable power supply.

In Example 13, the implantable sensor of Example 11 or Example 12 in which the flexible anchor assembly contacts an inner surface of the body lumen to anchor the implantable sensor within the body lumen.

Example 14 is a method of generating electrical power within the body of a patient by inserting an implantable medical device into the body. The implantable medical device has a housing including an exterior housing wall having an inner surface and an outer surface, the exterior housing wall defining an internal cavity and a flexible anchor assembly coupled to the housing. The flexible anchor assembly includes a first electrical conductor, a second electrical conductor, and a piezoelectric layer disposed between the first and second electrical conductors, the piezoelectric layer configured to displace in response to a bodily force applied to the implantable medical device and generate a voltage differential between the first and second electrical conductors. Power circuitry is configured to convert the voltage differential between the first and second conductors into an operating current for powering one or more components of the implantable medical device. The implantable medical device is operated within the body at a location that subjects the piezoelectric layer to a bodily force, causing a voltage differential between the first and second electrical conductors. The voltage differential is converted into an operating current for powering one or more components of the implantable medical device.

In Example 15, the method of Example 14 in which inserting the implantable medical device within a patient includes inserting the implantable medical device into a body lumen such that the implantable medical device will be exposed to periodic pressure pulses within the body lumen.

In Example 16, the method of Example 14 or Example 15 in which at least a portion of the flexible anchor assembly is configured to contact an interior portion of the body lumen to anchor the implantable medical device within the body lumen.

In Example 17, the method of any of Examples 14 to 16 in which the one or more components includes a rechargeable power source and the method further includes charging the rechargeable power source with the operating current.

In Example 18, the method of any of Examples 14 to 17 in which the one or more components includes sensing circuitry and the method further includes using the operating current to power the sensing circuitry.

In Example 19, the method of any of Examples 14 to 18 in which the one or more components includes wireless communication circuitry and the method further includes using the operating current to power the wireless communication circuitry.

In Example 20, the method of any of Examples 14 to 19 in which the flexible anchor assembly further includes a tissue attachment structure disposed at an end of the flexible anchor assembly opposite an end coupled to the housing, and the method further includes attaching the tissue attachment structure to a structure within a patient.

In Example 21, the method of any of Examples 14 to 20 in which the flexible anchor assembly includes a helical structure in which the piezoelectric layer includes a piezoelectric ribbon having a first surface and an opposing second surface. The first electrical conductor contacts the first surface of the piezoelectric ribbon and the second electrical conductor contacts the second surface of the piezoelectric ribbon.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
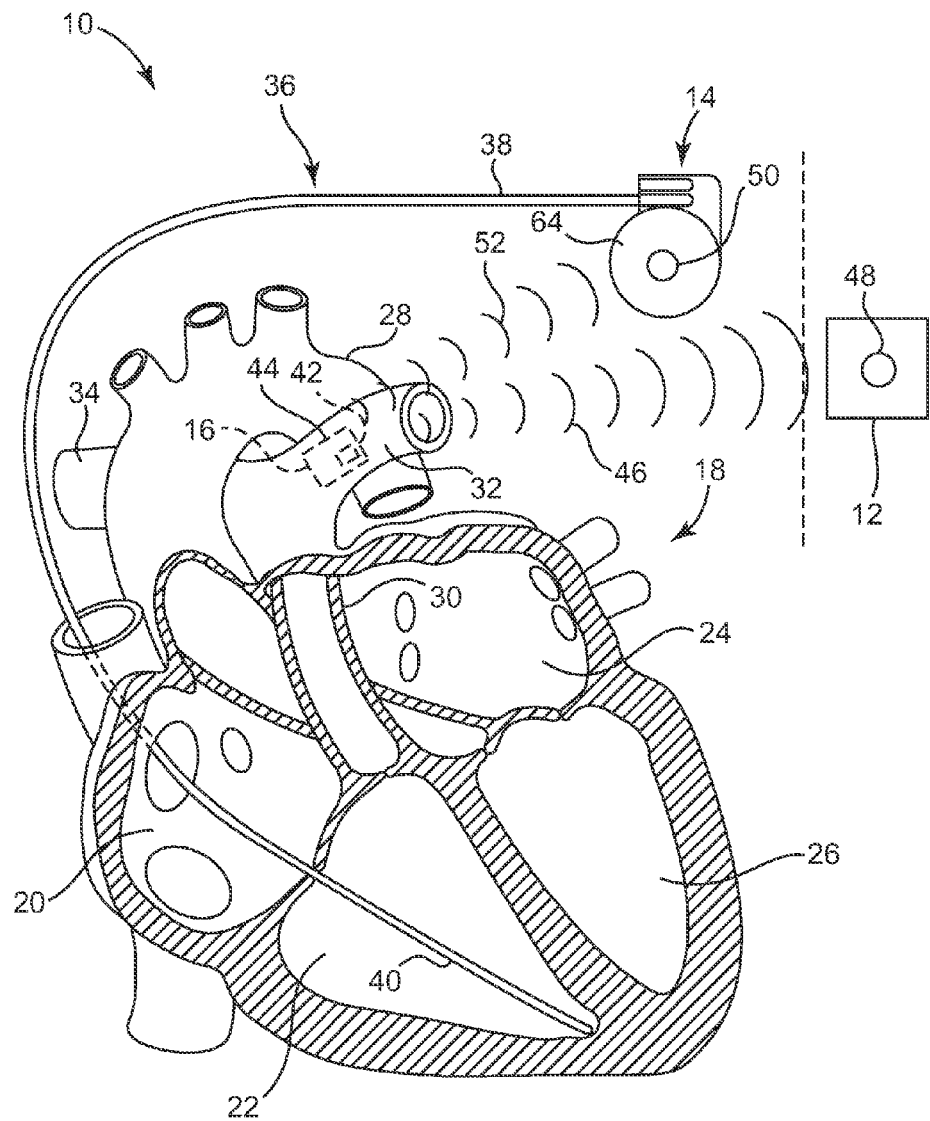
FIG. 1 is a schematic view of an illustrative system employing a remote implantable medical device (IMD) located within the body of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative system 10 employing a remote implantable medical device (IMD) located within the body of a patient. The system 10, illustratively a cardiac rhythm management system for providing cardiac rhythm management or cardiac disease management, includes an external monitor 12 (e.g., an external communicator, reader, or programmer), a pulse generator 14 implanted within the body, and at least one remote IMD 16 implanted deeply within the patient's body such as in one of the atria or ventricles of the patient's heart 18, or in one of the blood vessels leading into or from the heart 18. The heart 18 includes a right atrium 20, a right ventricle 22, a left atrium 24, a left ventricle 26, and an aorta 28. The right ventricle 22 leads to the main pulmonary artery 30 and the branches 32, 34 of the main pulmonary artery 30.

In the illustrative system 10 depicted, the pulse generator 14 is coupled to a lead 36 deployed in the patient's heart 18. The pulse generator 14 can be implanted subcutaneously within the body, typically at a location such as in the patient's chest or abdomen, although other implantation locations are possible. A proximal portion 38 of the lead 36 can be coupled to or formed integrally with the pulse generator 14. A distal portion 40 of the lead 36, in turn, can be implanted at a desired location within the heart 18 such as the right ventricle 22, as shown. Although the illustrative system 10 depicts only a single lead 36 inserted into the patient's heart 18, in other embodiments the system 10 may include multiple leads so as to electrically stimulate other areas of the heart 18. In some embodiments, for example, the distal portion of a second lead (not shown) may be implanted in the right atrium 20. In addition, or in lieu, another lead may be implanted in the left side of the heart 18 (e.g., in the coronary veins) to stimulate the left side of the heart 18. Other types of leads such as epicardial leads may also be utilized in addition to, or in lieu of, the lead 36 depicted in FIG. 1.

During operation, the lead 36 is configured to convey electrical signals between the heart 18 and the pulse generator 14. For example, in those embodiments where the pulse generator 14 is a pacemaker, the lead 36 can be utilized to deliver electrical therapeutic stimulus for pacing the heart 18. In those embodiments where the pulse generator 14 is an implantable cardiac defibrillator, the lead 36 can be utilized to deliver electric shocks to the heart 18 in response to an event such as ventricular fibrillation. In some embodiments, the pulse generator 14 includes both pacing and defibrillation capabilities.

The remote IMD 16 can be configured to perform one or more designated functions, including the sensing of one or more physiologic parameters within the body. Example physiologic parameters that can be measured using the remote IMD 16 can include, but are not limited to, blood pressure, blood flow, and temperature. Various electrical, chemical, magnetic, and/or sound properties may also be sensed within the body via the remote IMD 16.

In the embodiment of FIG. 1, the remote IMD 16 includes a pressure sensor implanted at a location deep within the body such as in the main pulmonary artery 30 or a branch of the main pulmonary artery 30 (e.g., in the left pulmonary artery 32 or the right pulmonary artery 34). An example of a pressure sensor suitable for use in sensing blood pressure in a pulmonary artery is described in U.S. Pat. No. 6,764,446, entitled "Implantable Pressure Sensors and Methods for Making and Using Them," which is incorporated herein by reference in its entirety for all purposes. In use, the remote IMD 16 can be used to aid in the prediction of decompensation of a heart failure patient and/or to aid in optimizing cardiac resynchronization therapy via the pulse generator 14 by monitoring blood pressure within the body. In some embodiments, the remote IMD 16 can be configured to sense, detect, measure, calculate, and/or derive other associated parameters such as flow rate, maximum and minimum pressure, peak-to-peak pressure, rms pressure, and/or pressure rate change.

The remote IMD 16 may be implanted in other regions of the patient's vasculature, in other body lumens, or in other areas of the body, and may include any type of chronically implanted device adapted to deliver therapy and/or monitor biological and chemical parameters, properties, and functions. The remote IMD 16 can be tasked, either alone or with other implanted or external devices, to provide various therapies or diagnostics within the body. In certain embodiments, for example, the remote IMD 16 is configured to sense intracardiac pressure, which can be used as feedback for providing pacing therapy to the patient's heart 18 via the lead 36 and pulse generator 14. Although a single remote IMD 16 is depicted in FIG. 1, multiple such devices can be implanted at various locations within the body for sensing or monitoring physiologic parameters and/or providing therapy at multiple regions within the body.

An acoustic communication link may be established to permit wireless communications between the remote IMD 16 and the external monitor 12, between the remote IMD 16 and the pulse generator 14, and/or between the remote IMD 16 and one or more other devices located inside or outside of the body. In the illustrative system 10 of FIG. 1, for example, an ultrasonic transducer 42 disposed within the housing 44 of the remote IMD 16 is configured to transmit an ultrasound signal 46 towards the external monitor 12. An example ultrasonic transducer suitable for use with the remote IMD 16 for transmitting and receiving ultrasound signals is described in U.S. Pat. No. 6,140,740, entitled "Piezoelectric Transducer," which is expressly incorporated herein by reference in its entirety for all purposes.

The external monitor 12 includes one or more ultrasonic transducers 48 configured to receive the ultrasound signal 46 and complete an acoustic link between the remote IMD 16 and the external monitor 12. In some cases, for example, the acoustic link established between the remote IMD 16 and the external monitor 12 can be used to wirelessly transmit sensor data, operational status information, and/or other information to the external monitor 12. An example telemetry system employing ultrasonic transducers is described in U.S. Pat. No. 7,024,248, entitled "Systems and Methods For Communicating With Implantable Devices," which is incorporated herein by reference in its entirety for all purposes.

In some embodiments, the ultrasonic transducer(s) 48 for the external monitor 12 may transmit an ultrasound signal to the remote IMD 16 to prompt the IMD 16 to perform a desired operation. In one embodiment, for example, the external monitor 12 may transmit an acoustic wake-up command to the remote IMD 16, causing the IMD 16 to activate from an initial, low-power state for conserving power usage to an active, energized state for taking one or more sensor measurements and transmitting sensor data to the external monitor 12, to the pulse generator 14, and/or to another device located inside or outside of the body. In some embodiments, the external monitor 12 may transmit an acoustic control signal that prompts the remote IMD 16 to wake up only a portion of the IMD 16 and transmit one or more ultrasonic pulses without activating the sensor circuitry within the IMD 16.

While the system 10 of FIG. 1 includes a remote IMD 16 that communicates with an external monitor 12, in other embodiments the remote IMD 16 communicates with other devices located inside or outside of the patient's body. As further shown in FIG. 1, for example, the remote IMD 16 may be in acoustic communication with the pulse generator 14, which can include one or more ultrasonic transducers 50 adapted to receive an ultrasound signal 52 transmitted by the remote IMD 16. In certain embodiments, the ultrasonic transducer(s) 50 are coupled to an interior portion of a can that encloses the various components of the pulse generator 14. In other embodiments, the ultrasonic transducer(s) 50 are located outside of the can 54, on a header of the can 54, or are coupled to the pulse generator 14 through a feedthrough provided on the can 54.

Although the system 10 depicted in FIG. 1 shows an acoustic link between the remote IMD 16 and an external monitor 12, and/or between the IMD 16 and a pulse generator 14, in other embodiments an acoustic link can be established between the remote IMD 16 and another device implanted within the body. In some embodiments, for example, an acoustic link can be established between a primary IMD 16 and one or more secondary IMDs 16 implanted within the body.

Figure 2:
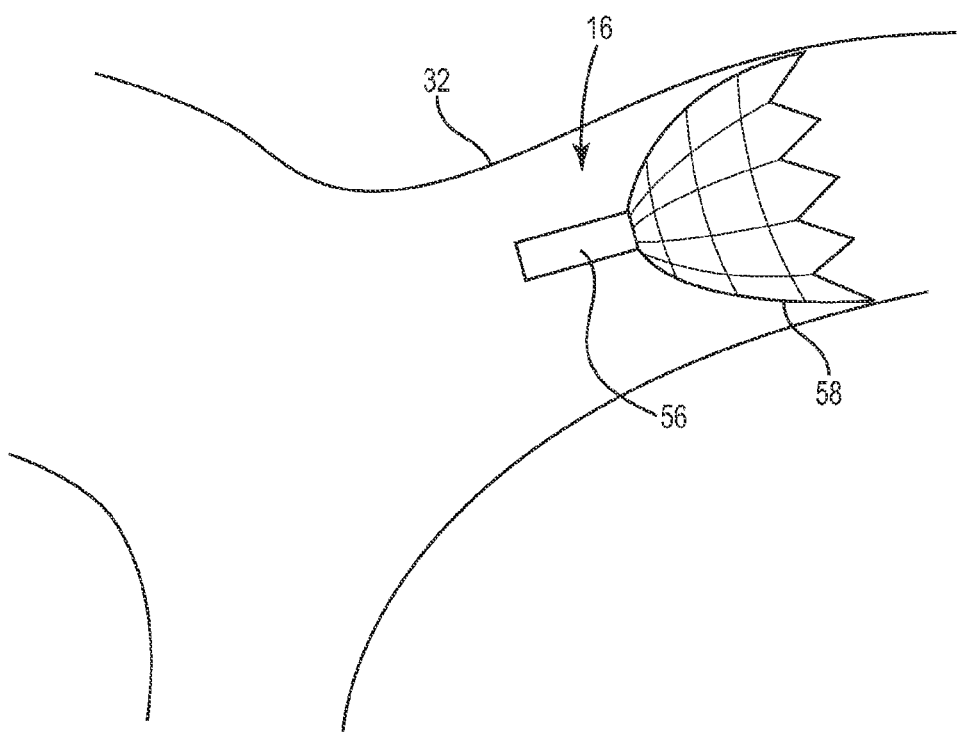
FIG. 2 is an enlarged schematic view of the IMD of FIG. 1, showing the IMD implanted in the patient's left pulmonary artery.

FIG. 2 is an enlarged schematic view of the remote IMD 16, showing the remote IMD 16 implanted in the patient's left pulmonary artery 32. As illustrated, the remote IMD 16 includes a sensor module 56 coupled to an anchor assembly 58. While the sensor module 56 is shown as having a single module housing, it will be appreciated that in some embodiments the sensor module 56 may have two or more housings or structures coupled together. In one embodiment, for example, the sensor module 56 may include a sensor module housing that includes one or more components for sensing one or more physiologic parameters, and a power supply module housing coupled to the sensor module housing and including a battery for providing power to one or more components of the sensor module.

The anchor assembly 58 is coupled to the sensor module 56 and, upon deployment at a target location within the vasculature, is adapted to radially expand such that it contacts and frictionally engages the vessel walls, securing and stabilizing the IMD 16 at the target location. In some examples, the anchor assembly 58 is made from a shape memory material such as Nitinol, and is configured to radially self-expand upon deployment from a delivery member such as, for example, a delivery catheter or sheath. Alternatively, and in other embodiments, the anchor assembly 58 may be radially expanded within the vessel via a deployment member such as a balloon catheter.

In some embodiments, the anchor assembly 58 is configured to locate the sensor module 56 at a position that exposes the sensor module 56 to pulsitile blood pressure within the vessel. In some embodiments, the sensor module 56 is configured to measure pulsitile blood pressure, which refers to the rhythmic blood pressure pulses resulting from the heart 18 beating. As illustrated, the sensor module 56 is deployed at a position in which the sensor module 56 is offset a small distance from the vessel wall. This location permits a pressure calibration catheter such as a Swanz Ganz catheter to be inserted adjacent the sensor module for calibration purposes.

Figure 3:
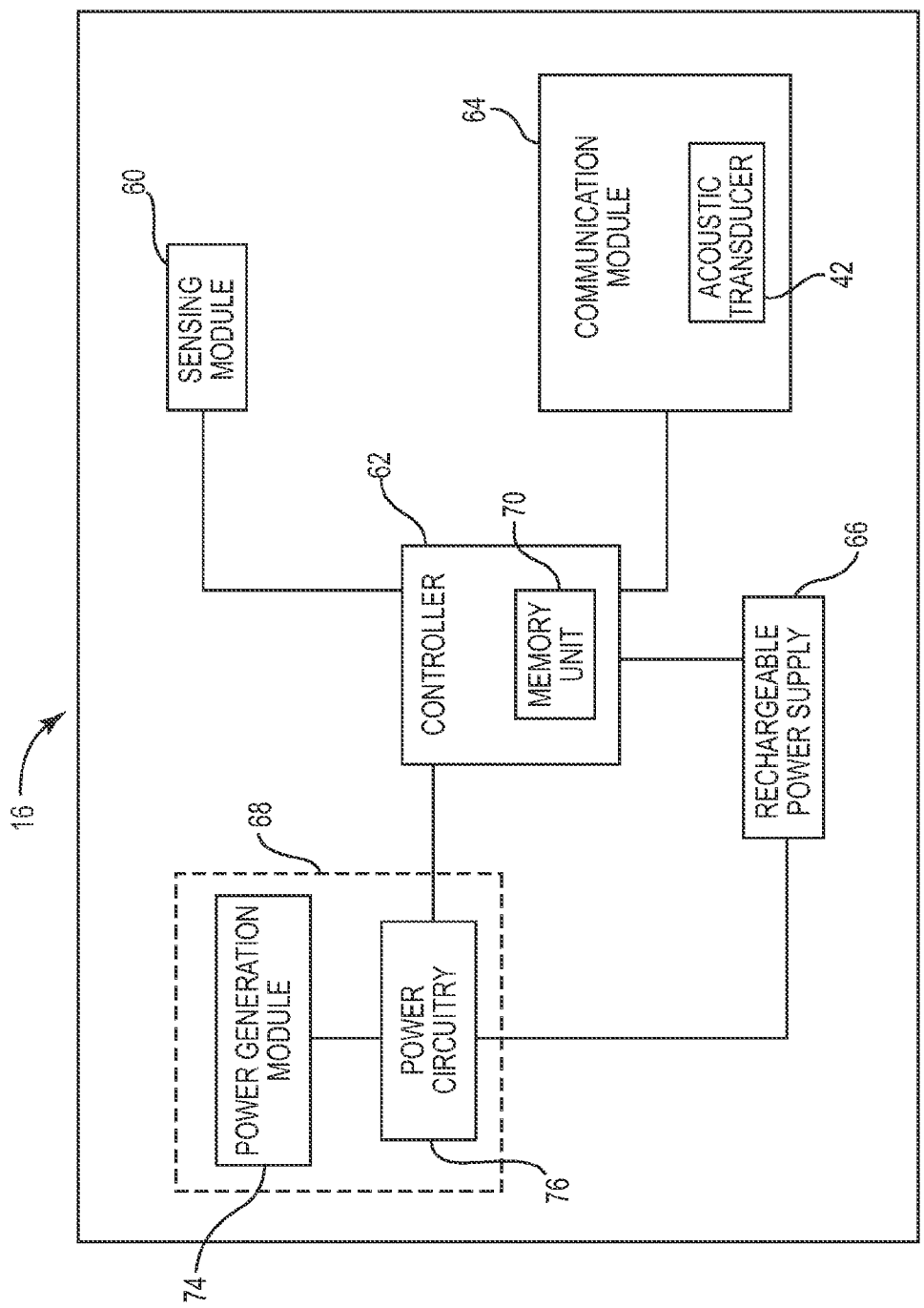
FIG. 3 is a schematic block diagram showing several illustrative components disposed within the IMD of FIGS. 1-2.

FIG. 3 is a schematic block diagram showing several illustrative components disposed within the IMD 16 of FIGS. 1-2. As shown in FIG. 3, and in some embodiments, the IMD 16 includes a sensing module 60, a controller 62, a communication module 64, a rechargeable power supply 66, and a power module 68.

The sensing module 60 is configured to sense, detect, measure, calculate, and/or derive intracardiac blood pressure as well as other associated parameters such as flow rate, maximum and minimum pressure, peak-to-peak pressure, rms pressure, and/or pressure rate change. In certain embodiments, for example, the sensing module 60 includes a pressure sensor adapted to measure blood pressure in a body vessel. In one embodiment, the remote IMD 16 is implanted in a pulmonary artery of the patient, and the sensing module 60 is adapted to sense blood pressure within the artery. In some embodiments, the sensing module 60 performs functions related to the sensing of one or more other physiologic parameters within the body such as, for example, temperature.

In some embodiments, the controller 62 is configured to control operation of the sensing module 60, the communication module 64 and the power module 68. In some cases, the sensing module 60 spends significant time in an energy-conserving or sleep mode, and the controller 62 may periodically wake up the sensing module 60 so that the sensing module 60 can sense desired physiological parameters. In some embodiments, as illustrated, the controller 62 may include a memory unit 70 that can be used to store sensed physiological parameters until such time as they can be transmitted by the communication module 64 to the external monitor 12, pulse generator 14, or other communicating device.

The communication module 64 includes an acoustic transducer 42 that is configured to provide communications between the IMD 16 and the external monitor 12 (FIG. 1) and/or the pulse generator 14 (FIG. 1). In some embodiments, the acoustic transducer 42 includes one or more piezoelectric transducer elements configured to transmit and receive acoustic signals. In a reception mode of operation, the acoustic transducer 42 can be configured to receive a control signal transmitted from the external monitor 12 and/or the pulse generator 14. In a transmit mode of operation, the acoustic transducer 42 is configured to transmit an ultrasound signal to the external monitor 12 or to the pulse generator 14. In some embodiments, the communication module 64 transmits, via the acoustic transducer 42, sensed data immediately and in real time. If the controller 62 includes a memory unit 70, as discussed above, the communication module 64 may transmit sensor data at a later time using sensed data that is stored within the memory unit 70 along with timing markers associated with such data.

In some embodiments, the rechargeable power supply 66 includes a rechargeable battery or batteries that are configured to permit multiple recharging cycles. In some embodiments, the rechargeable power supply 66 includes one or more power capacitors that can be used to store an electrical charge. The rechargeable power supply 66 provides power to the sensing module 60, the controller 62, and the communication module 64, and may provide power to other components not expressly discussed herein.

In some instances, the rechargeable power source 66 can be recharged remotely by remotely energizing an acoustic transducer to generate power that can be used to recharge the rechargeable power supply 66. In particular, the external monitor 12 can be used to transmit an acoustic wave that can be received by an acoustic transducer within the IMD 16 (such as the acoustic transducer 42 within the communication module 64) and converted into electrical energy for powering one or more components of the IMD 16 and/or recharging the rechargeable power supply 66.

In some embodiments, as illustrated, the power module 68 includes a power generation module 74 as well as power circuitry 76. In brief, the power generation module 74 is configured to generate electrical power and the power circuitry 76 is configured to convert or regulate the generated electrical power in a way that the power can be used to recharge the rechargeable power source 66 and/or power at least some of the other components within the IMD 16, including the sensing module 60, the controller 62, and the communication module 64.

In some embodiments, and as discussed further herein, the power generation module 74 is configured to capture or harness a time-varying electrical field that results from displacing or otherwise straining a piezoelectric material. If a piezoelectric material is displaced or stressed, an electrical field results. This is known as the piezoelectric effect. The electrical field can create a voltage differential between first and second electrical conductors that sandwich the piezoelectric material. If the piezoelectric material is displaced or strained in a time-dependent manner, the resulting voltage differential between the first and second electrical conductors is also time-dependent. In some embodiments, the power circuitry 76 is configured to convert the voltage differential into an electrical current. In some embodiments, the power circuitry 76 includes a rectifier circuit for converting the time-dependent voltage differential into a DC electrical current.

In some embodiments, the power generation module 68 is configured to capture kinetic energy present within or near the patient's vasculature. As the heart 18 beats, there is a rhythmic fluctuation in blood pressure within the vessel that can be captured by the power generation module 68. Due to the piezoelectric effect, displacement of the piezoelectric material in response to the mechanical stress provided on the material by the fluctuation in blood pressure produces a voltage differential between electrical conductors sandwiching the piezoelectric material. Since the forces applied to the piezoelectric material are time-dependent, the resulting voltage differential also varies with time. This time-dependent voltage differential can be converted into an electrical current by the power circuitry 76, as noted above.

Figure 4:
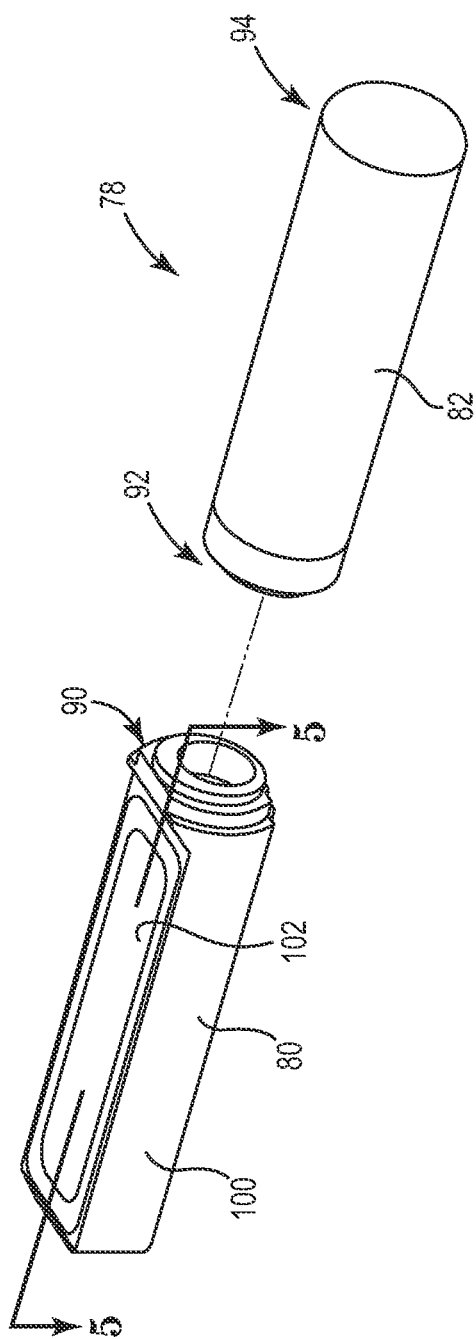
FIG. 4 is an exploded perspective view of an implantable sensor that is an illustrative example of the IMD of FIGS. 1-3.

FIG. 4 is an exploded perspective view of an implantable sensor 78 that is an illustrative example of the IMD 16 of FIGS. 1-3. In the illustrated embodiment, the implantable sensor 78 includes a sensor module 80 and a power storage module 82. In some embodiments, the sensor module 80 includes at least some of the components described above with respect to the IMD 16. In some embodiments, the power storage module 82 includes a rechargeable battery and/or a power capacitor. In some embodiments, the sensor module 80 is configured to fixedly connect to the power storage module 82 and thus has an end 90 that is configured to mate with a corresponding end 92 of the power storage module 82. Similarly, as illustrated, the power storage module 82 can have an end 94 that connects to a portion of an anchor assembly.

In the illustrated embodiment, the sensor module 80 includes a housing 100. A portion of the housing 100 includes a flexible diaphragm 102 and can be formed of titanium or other biocompatible material. The remaining portions of the housing 100 includes a number of rigid housing walls. In some embodiments, the diaphragm 102 is thinner than the rest of the housing 100 so that the diaphragm 102 can flex or displace in response to blood pressure pulses impinging on the diaphragm 102. This protects the components within the housing 100 while permitting one or more of the components (such as the sensing module 60 of FIG. 3) within the housing 100 to detect the blood pressure pulses. In some embodiments, the diaphragm 102 is configured to be secured to the housing 100 after the internal components of the implantable sensor 78 have been installed.

Figure 5:
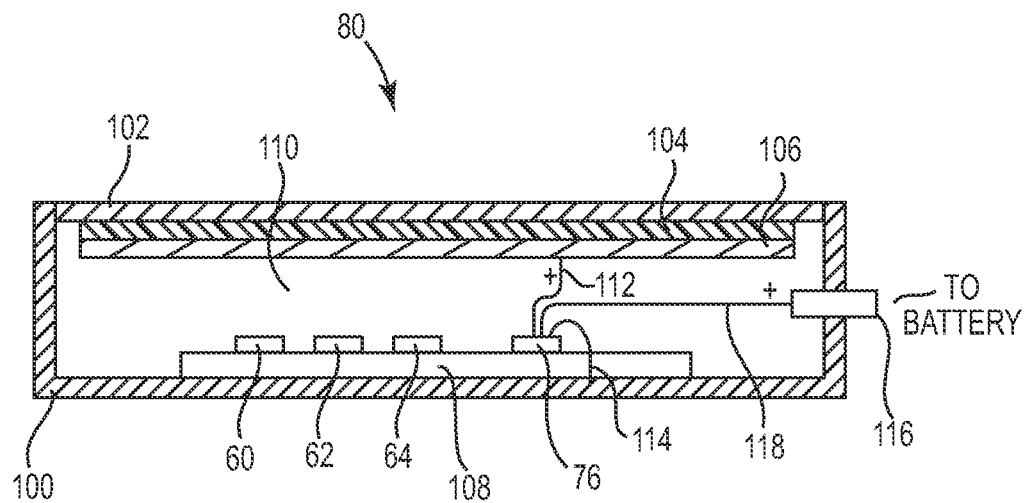
FIG. 5 is a schematic cross-sectional view of the implantable sensor of FIG. 4, showing the incorporation of the power generation module into the IMD.

FIG. 5 is a schematic cross-sectional view of the sensor module 80 taken along line 5-5 of FIG. 4, showing the incorporation of the power generation module 68 of FIG. 3 into the sensor module housing 100. In the illustrated embodiment, the diaphragm 102 includes a piezoelectric layer 104 and an electrical conductor 106. In some embodiments, the diaphragm 102 is metallic (such as titanium, as discussed above) and thus functions as an electrical conductor. The piezoelectric layer 104 is sandwiched or interposed between the diaphragm 102 and the electrical conductor 106. As a result, the diaphragm 102 and the electrical conductor 106 are configured to capture a voltage differential that results, as discussed above, when the piezoelectric layer 104 flexes or otherwise displaces in response to applied force.

In the illustrated embodiment, the sensor module 80 has a circuit board 108 that includes at least some of the components discussed with respect to FIG. 3, such as the sensing module 60, the controller 62, the communication module 64, and the power circuitry 76. While each of these components are generically illustrated on the circuit board 108, it will be appreciated that one or more of these components may be manifested in software and/or hardware that are located on distinct boards that are electrically connected to the circuit board 108.

The housing 100 defines an interior cavity 110 that the circuit board 108 is disposed in. In some embodiments, the interior cavity 110 is filled with a fluid (e.g. air) in order to transmit pressure pulses exterior to the housing 100 to the sensing module 60. When the sensor module 80 is exposed to rhythmic blood pressure pulses within the vessel (such as the left pulmonary artery 32 shown in FIG. 2), the diaphragm 102 displaces or otherwise flexes into the interior cavity 110.

As the diaphragm 102 moves, the piezoelectric layer 104 that is secured to the diaphragm 102 also moves. The rhythmic movement of the piezoelectric layer 104 (as a result of the rhythmic blood pressure pulses) generates a time-varying electric field that causes a voltage differential to form between the two electrical conductors on either side of the piezoelectric layer. The sensor module 80 includes a positive lead 112 that extends from the electrical conductor 106 to the power circuitry 76. In some embodiments, the diaphragm 102 (functioning as the other electrical conductor) is grounded to the housing 100. Thus, a negative lead 114 extends from the housing 100 to the power circuitry 76. In the illustrated embodiment, the diaphragm 102 and the electrical conductor 106 electrically conduct the aforementioned voltage differential and transmit a current to the power circuitry 76 via the positive lead 112 and the negative lead 114.

In some embodiments, the sensor module 76 includes a positive electrical post 116 and a positive lead 118 that electrically couples the electrical post 116 to the power circuitry 76. As the power circuitry 76 converts the time-dependent voltage differential into an electrical current, the current may be provided to the positive electrical post 116 via the positive lead 118. From the positive electrical post 116 (and a negative path grounded to the housing 100), the generated electrical current is provided to other components such as the rechargeable power supply 66 (FIG. 3). In some embodiments, the circuit board 108 includes circuitry that directs at least some of the generated electrical current to other components such as the sensing module 60, the controller 62, and the communication module 64.

Figure 6:
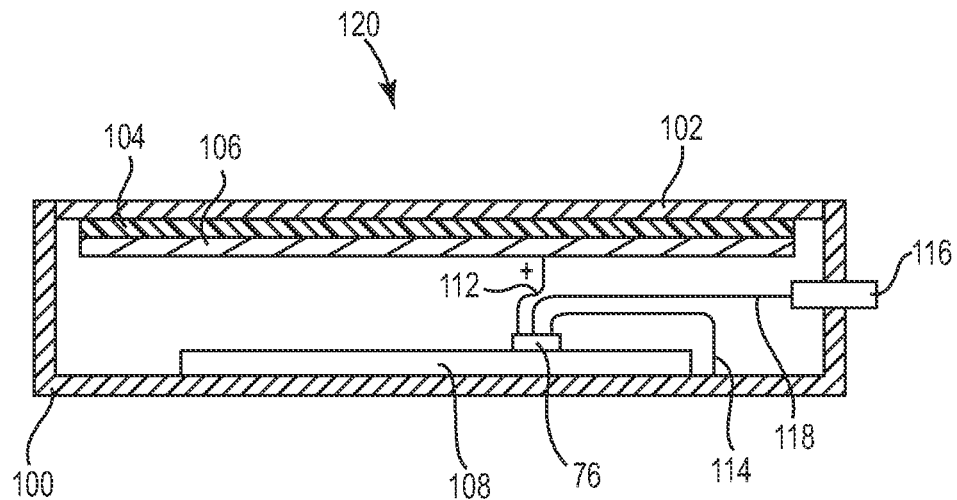
FIG. 6 is a schematic cross-sectional view of an implantable power station that can be used with the IMD of FIGS. 1-3.

FIG. 6 is a schematic cross-sectional view of an implantable power station 120 that is similar to the sensor module 80 of FIG. 4, but that does not include some of the internal components of the sensor module 80. Implantable power station 120 may comprise, for example, a power station that is a separate component from an implantable medical device, but which generates power from a position within the body for powering and/or recharging the implantable medical device. In the illustrated embodiment, the implantable power station 120 has a housing 100 and a diaphragm 102 that are similar to that discussed with respect to the sensor module 80. The piezoelectric layer 104 is disposed along a surface of the diaphragm 102 and an electrical conductor 106 is disposed along the piezoelectric layer 104 such that the piezoelectric layer 104 is sandwiched or interposed between the diaphragm 102 (functioning as a first conductor) and the electrical conductor 106 (functioning as a second conductor).

The implantable power station 120 includes a circuit board 108 having disposed thereon the power circuitry 76. The leads 112, 114 electrically connect the power circuitry 76 to the electrical conductors that harness the time-dependent voltage differential that results when, as discussed above, the piezoelectric layer 104 moves and/or displaces. In some embodiments, the power circuitry 76 converts the time-dependent voltage differential into an electrical current that can be used for recharging a rechargeable power supply and/or for powering one or more components in an attached implantable medical device. Power is provided via the positive lead 118 to the positive electrical post 116 and via a grounded connection to the housing 100, as discussed previously.

In some embodiments, the implantable power station 120 is coupled to one or more components of an implantable medical device having power needs. In an illustrative embodiment, and with reference to the implantable sensor 78 described with respect to FIG. 4, the implantable structure 120 can be coupled between the sensor module 80 and the power storage module 82. In some embodiments, the implantable power station 120 is coupled between the power storage module 82 and the anchor assembly 84. It will be appreciated that, depending on the power requirements of the implantable medical device, two or more of the implantable power stations 120 can be electrically coupled, either in series or in parallel, to an implantable medical device.

Figure 7:
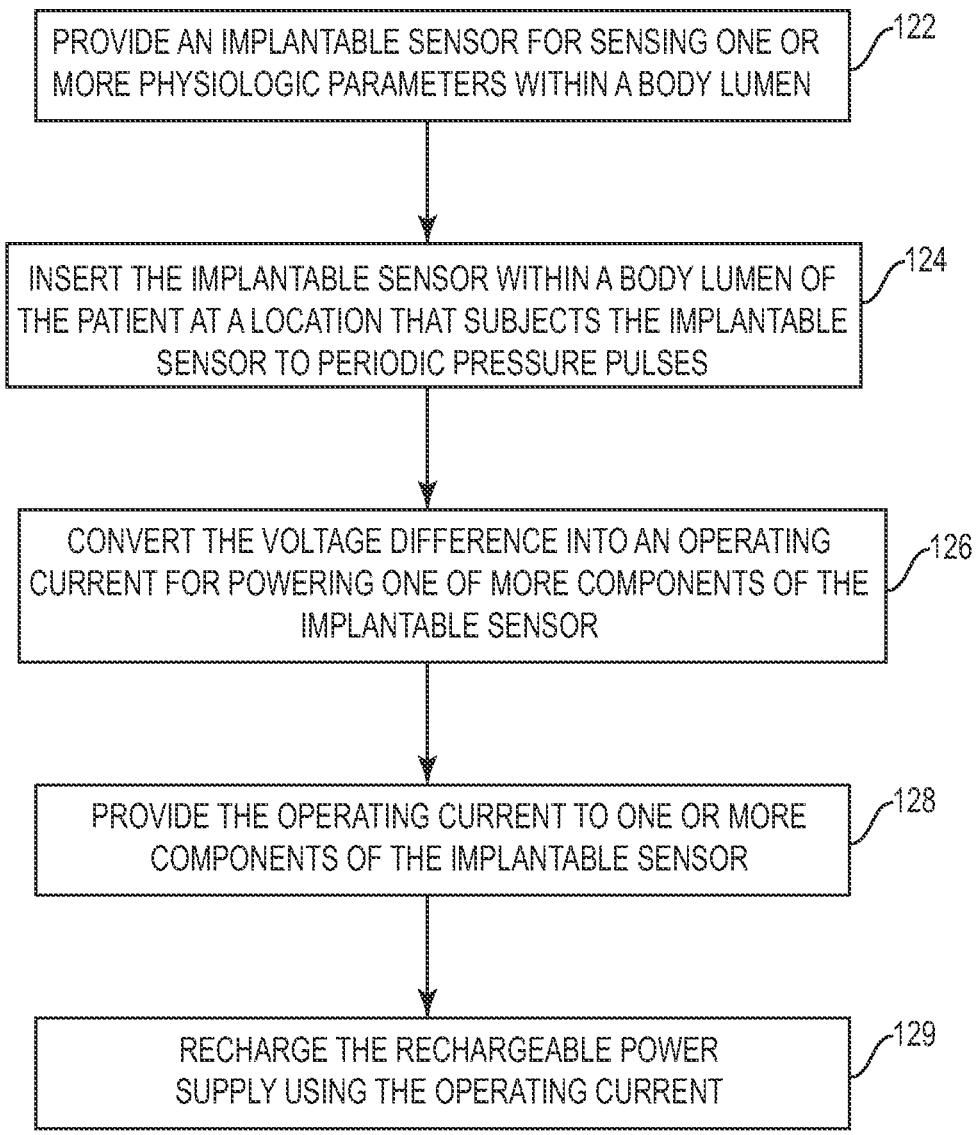
FIG. 7 is a flow diagram illustrating a method that can be carried out using the implantable sensor of FIG. 4.

FIG. 7 is a flow diagram illustrating a method that can be carried out using an implantable medical device such as, for example, the implantable sensor 78 described with respect to FIG. 4. The method begins by providing at block 122 an implantable sensor, such as implantable sensor 78, that is configured to sense one or more physiologic parameters within a body lumen. In some embodiments, the body lumen may be a pulmonary artery such as the left or right pulmonary artery, although other body lumens are contemplated. At block 124, the implantable sensor is inserted into a body lumen at a location that subjects the implantable sensor to periodic pressure pulses within the body lumen. As discussed above, the periodic pressure pulses cause the diaphragm 102 (and hence the piezoelectric layer 104) to displace, thereby creating a time-dependent electric field that causes a time-varying voltage differential to form between two electrical conductors adjacent to the piezoelectric layer 104.

Control passes to block 126, where the aforementioned time-varying voltage differential is converted into an operating current for powering and/or recharging one or more components of the implantable sensor 78. In some embodiments, the time-varying voltage differential is converted into an operating current via the power circuitry 76 (FIG. 3). At block 128, the operating current is provided to one or more components of the implantable sensor 78. In some embodiments, and with particular reference to FIGS. 3 and 5, the operating current is used to power one or more of the sensing module 60, the controller 62, or the communication module 64. In some embodiments, at least some of the operating current may be used to recharge the rechargeable power supply 66, as indicated at block 129.

Figure 8:
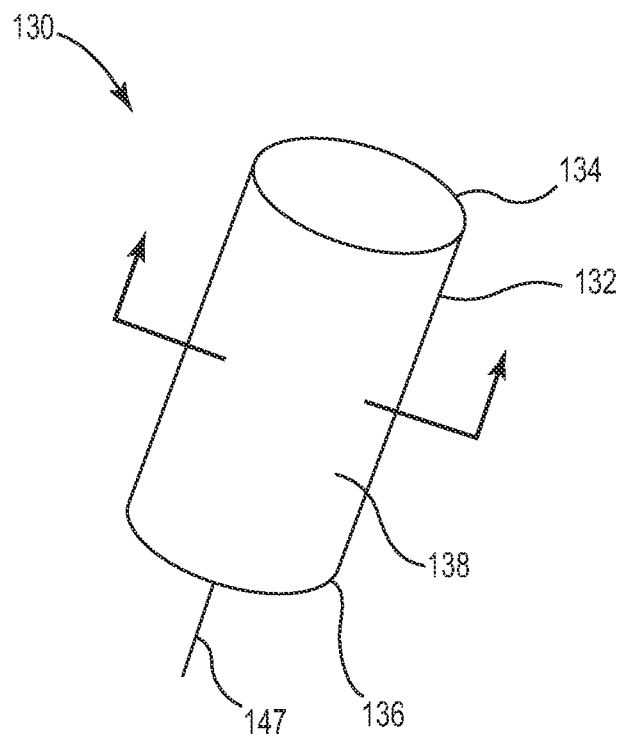
FIG. 8 is a perspective view of an IMD.
Figure 9:
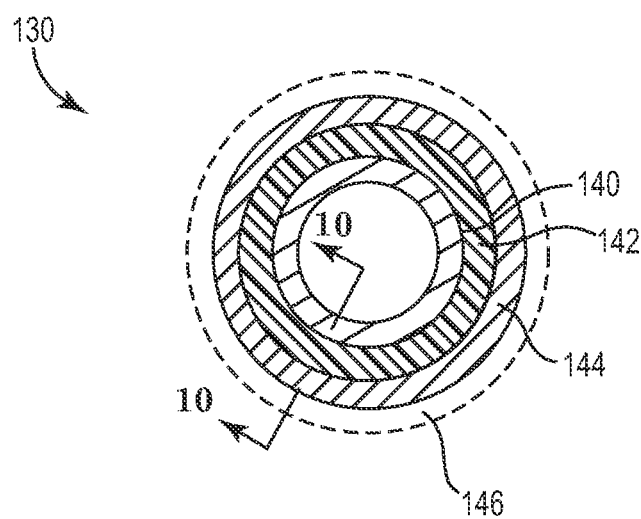
FIG. 9 is a cross-section taken along line 9-9 of FIG. 8.

In some embodiments, as discussed with respect to FIGS. 4 through 6, the implantable medical device has a rigid or substantially rigid housing such as the housing 100. However, in some embodiments, the entire housing may be flexible and thus can be used to generate electrical power. FIGS. 8 and 9 show an implantable medical device 130 in which the piezoelectric material has been added to at least a substantial portion of the exterior of the implantable medical device 130, thereby increasing the effective surface that is used to generate electrical power.

FIG. 8 is a perspective view of the implantable medical device 130. FIG. 9, in turn, is a cross-section of the device 130 taken along line 9-9 of FIG. 8, showing several piezoelectric and electrically conductive layers disposed within the implantable device 130. With reference to FIG. 8, it can be seen that the implantable medical device 130 includes a cylindrically shaped housing 132 having a first end 134, a second end 136, and an outer surface 138 that extends from the first end 134 to the second end 136.

As can be further seen in FIG. 9, the implantable medical device 130 includes a housing wall 140 that forms the outer surface 138. In some embodiments, as illustrated, the implantable medical device 130 includes at least some features of the power module 68 of FIG. 3, and thus can generate electrical power that is stored and/or used to power at least some components within the implantable medical device 130. In some embodiments, the housing wall 140 is formed of titanium or another conductive material, and therefore functions as a first electrical conductor. A piezoelectric layer 142 is wrapped or otherwise disposed about the housing wall 140. A second electrical conductor 144 is wrapped or otherwise disposed about the piezoelectric layer 142. In some embodiments, a protective layer 146 formed of a biocompatible material is disposed about the second electrical conductor 144.

The implantable device 130 may be implanted within a patient at a location that subjects the implantable medical device 130 to forces that cause the piezoelectric layer 142 to displace. In some embodiments, for example, the implantable medical device 130 can be subjected to physiologic forces such as muscle movement or periodic pressure pulses within the vasculature that cause the outer surface 138 of the implantable medical device 130 to displace inwardly. Movement of the piezoelectric layer 142 creates a voltage differential between the housing wall 140 and the second electrical conductor 144. Circuitry such as the power circuitry 76 of FIG. 3 may be disposed within the implantable medical device 130 to convert the voltage differential into an electrical current for powering the implantable medical device 130 and/or for recharging a power supply within the device 130.

In some embodiments, the implantable medical device 130 is a pacing or therapeutic device, and thus includes one or more pacing electrodes 147. At least some of the electrical current generated by movement of the piezoelectric layer 142 may be provided to the one or more pacing electrodes 147. Alternatively, or in addition, the implantable medical device 130 may include a rechargeable battery or a power capacitor that can be charged via the electrical current generated by the movement of the piezoelectric layer 142 when the current is not otherwise needed to provide pacing therapy.

Figure 10:
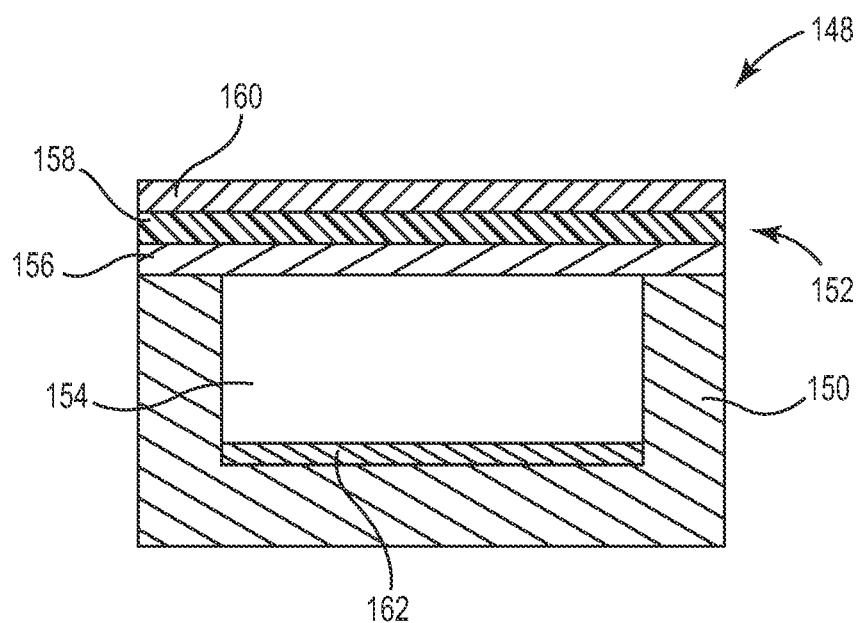
FIG. 10 is a schematic view of a capacitive pressure sensor having a sensing mode and a power generation mode that can be disposed within an IMD.

In the embodiments discussed with respect to FIGS. 5-6 and 8-9, the power generation module 58 (FIG. 3) is provided as part of the housing (such as the housing 100) of the implantable device. In some embodiments, however, the power generation module 68 may be manifested as one or more distinct elements that are disposed within the interior (such as the interior cavity 110 in FIG. 5) of the sensor module 80. FIG. 10 provides an example of a capacitive pressure sensor that, in addition to sensing one or more physiologic parameters such as blood pressure, can also be operated in a power generation mode to generate electrical power that can be used to power one or more components of an implantable medical device and/or to recharge a rechargeable power source.

FIG. 10 is a schematic view of a capacitive pressure sensor 148 having a sensing mode and a power generation mode. As illustrated, the capacitive pressure sensor 148 includes a body 150 and a flexible diaphragm 152. The body 150 defines a cavity 154 into which the flexible diaphragm 152 can displace when subjected to external forces. It will be appreciated that the capacitive pressure sensor 148 will be disposed within a sensor module such as the sensor module 80 of FIG. 4 in such a way so as to be exposed to periodic pressure pulses exterior to the sensor module 80. For example, the interior cavity 110 can be filled with a fluid such as a non-compressible fluid that transmits movement of the diaphragm 102 (FIG. 4) to components disposed within the interior cavity 110.

As illustrated, the flexible diaphragm 152 is a multi-layer structure that includes a first electrical conductor 156, a piezoelectric layer 158 disposed adjacent to the first electrical conductor 156, and a second electrical conductor 160 disposed adjacent to the piezoelectric layer 158 such that the piezoelectric layer 158 is sandwiched or interposed between the first electrical conductor 156 and the second electrical conductor 160. Changes in pressure within the interior cavity 110 cause the piezoelectric layer 158 to displace, which in turn creates a voltage differential between the first electrical conductor 156 and the second electrical conductor 160. Circuitry such as the power circuitry 76 of FIG. 3 converts the voltage differential into an electrical current that can be used to recharge a rechargeable power supply such as rechargeable power supply 66 and/or to power one or more components within the IMD 16.

The capacitive pressure sensor 148 also includes a lower electrical conductor 162 disposed within the cavity 154. A controller such as the controller 62 discussed with respect to FIG. 3, for example, can be configured to selectively connect or disconnect one or more of the first electrical conductor 156, the second electrical conductor 160, and the lower electrical conductor 162 from the power circuitry 76. When the lower electrical conductor 162 is electrically switched off, the capacitive pressure sensor 148 operates in a power generation mode and time-dependent movement of the piezoelectric layer 158 causes a varying voltage differential between the first electrical conductor 156 and the second electrical conductor 160. This varying voltage differential can be converted into an electrical current that can be used to power one or more components and/or used to recharge a rechargeable power supply such as the rechargeable power supply 66.

When the second electrical conductor 160 is electrically switched off, the capacitive pressure sensor 148 operates in a sensing mode and time-dependent movement of the flexible diaphragm 152 creates a varying capacitance between the first electrical conductor 156 and the lower electrical conductor 162. This varying capacitance can be interpreted or converted, such as by the controller 62, into a value that is representative of a pressure exterior to the capacitive pressure sensor 148.

In some embodiments, in order to capture electrical energy from a rhythmic fluctuation in capacitance or other source, it may be useful to sample a voltage across the capacitance in synch with a period of the changing capacitance. In doing so, it may be useful to generate a clock signal that is synchronous with the capacitive signal. In some cases, the clock signal may be synchronous with a rhythmic blood pressure. The clock signal may be generated in several illustrative manners.

In some embodiments, a clock signal may be generated by using a piezoelectric pressure transducer or acoustic transducer that is subjected to the blood pressure signal. A voltage signal from the transducer may be amplified using a high gain amplifier, which will output a saturated voltage signal with high edge rates. The transducer and amplifier may be connected in a differential configuration or in a single-ended configuration utilizing a single-ended amplifier. In some cases, a charge amplifier may be used instead of a voltage amplifier.

In some embodiments, a clock signal may be generated using a comparator. The voltage signal from the transducer may be applied to one input of the comparator while the other input may be connected to a DC voltage level (such as ground). The comparator will output a square wave signal that is synchronous with the input voltage signal and is suitable for use as a clock signal. In some embodiments, a low-pass filter may be used to produce the DC voltage level input to the comparator.

Figure 11:
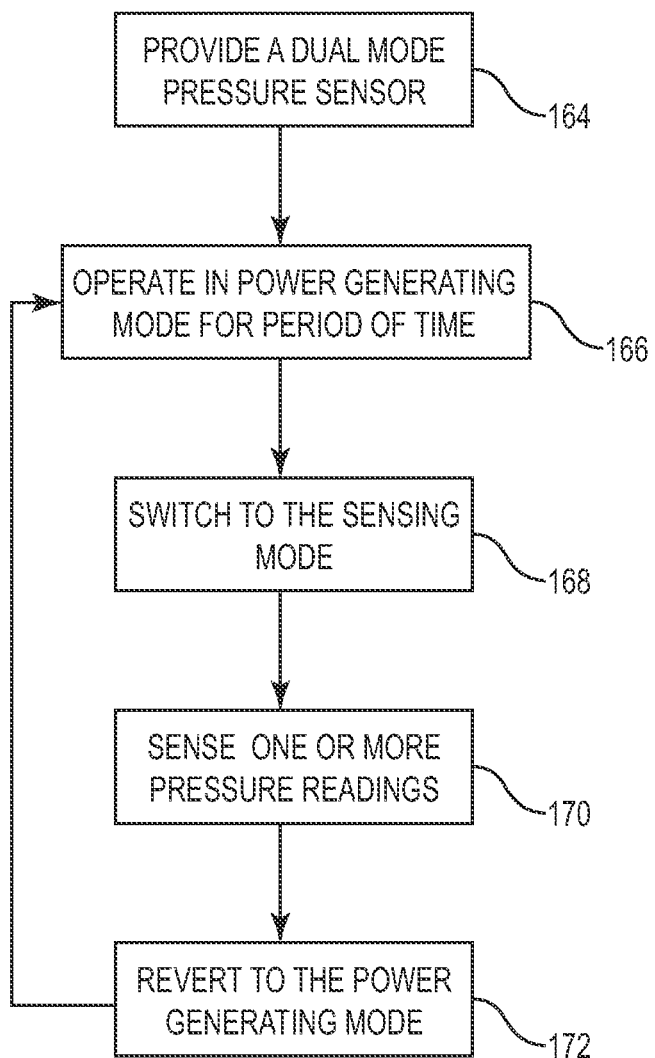
FIG. 11 is a flow diagram illustrating a method that can be carried out using the capacitive pressure sensor of FIG. 10.

FIG. 11 is a flow diagram illustrating a method that can be carried out using the capacitive pressure sensor 148 of FIG. 10. The method begins generally at block 164, where a dual mode pressure sensor such as the capacitive pressure sensor 148 of FIG. 10 is provided. The dual mode pressure sensor is operated in a power generating mode for a period of time, as generally indicated at block 166. In some embodiments, the dual mode pressure sensor 148 is operated in the power generating mode for a substantial length of time. For example, over the period of a day, the dual mode pressure sensor 148 may operate in the power generating mode for 23 hours or more, permitting the dual mode pressure sensor 148 to generate electrical power when not actively sensing.

At block 168, the dual mode pressure sensor 148 switches to a sensing mode and senses one or more pressure readings, as generally indicated at block 170. In some embodiments, the dual mode pressure sensor 148 may spend a relatively insubstantial length of time in the sensing mode. For example, the dual mode pressure sensor 148 may spend several seconds to several minutes in the sensing mode per hour, or per 24 hour day. Once one or more sensor measurements have been taken, the dual mode pressure sensor 148 may then revert back to the power generating mode at block 172. In some embodiments, as illustrated, control may revert to block 166, where the dual mode pressure sensor 148 repeats the previous steps.

Figure 12:
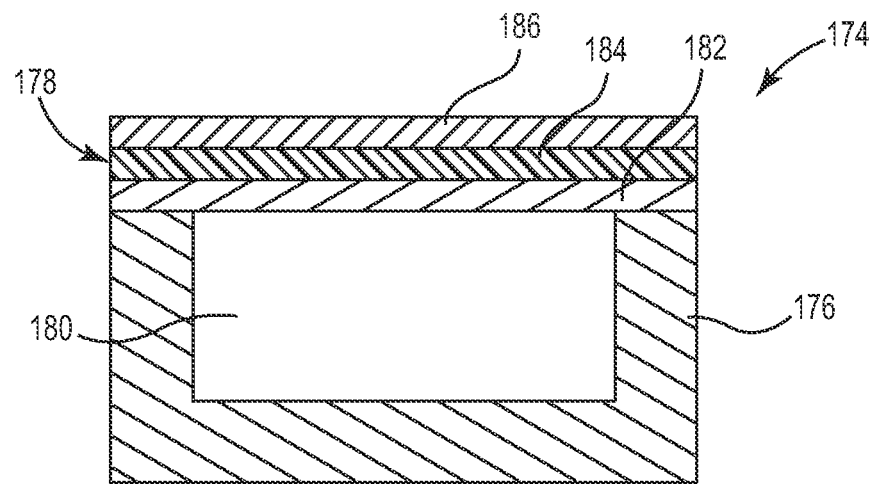
FIG. 12 is a schematic cross-sectional view of a power generator.

FIG. 12 is a schematic cross-sectional view of a power generator 174 in accordance with another illustrative embodiment of the power generation module 74 of FIG. 3. The power generator 174 can be provided as a component within an implantable device to generate power to meet at least some of the power requirements of the implantable device. In some embodiments, for example, the power generator 174 may provide power to one or more of the sensing module 60, the controller 62 or the communication module 64, and/or to recharge a rechargeable power supply such as the rechargeable power supply 66 of FIG. 3.

As shown in FIG. 12, the power generator 174 includes a body 176 and a flexible diaphragm 178. The body 176 defines a cavity 180 into which the flexible diaphragm 178 can displace in response to forces applied to the flexible diaphragm 178. For example, when the power generator 174 is provided as a component within the interior cavity 110 of the implantable pressure sensor 78, the flexible diaphragm 178 can be configured to displace in response to pressure pulses that are communicated into the interior cavity 110 of the implantable pressure sensor 78 from the surrounding vasculature.

The flexible diaphragm 178 includes several layers. In some embodiments, for example, the flexible diaphragm 178 includes a first electrical conductor 182, a piezoelectric layer 184 disposed adjacent to the first electrical conductor 182, and a second electrical conductor 186 disposed adjacent to the piezoelectric layer 184. In some embodiments, the piezoelectric layer 184 is sandwiched or interposed between the first electrical conductor 182 and the second electrical conductor 186 such that rhythmic displacement of the piezoelectric layer 184 causes a time-dependent voltage differential between the first electrical conductor 182 and the second electrical conductor 186 that can be converted into an electrical current for powering one or more components and/or to recharge a rechargeable power supply.

Figure 13:
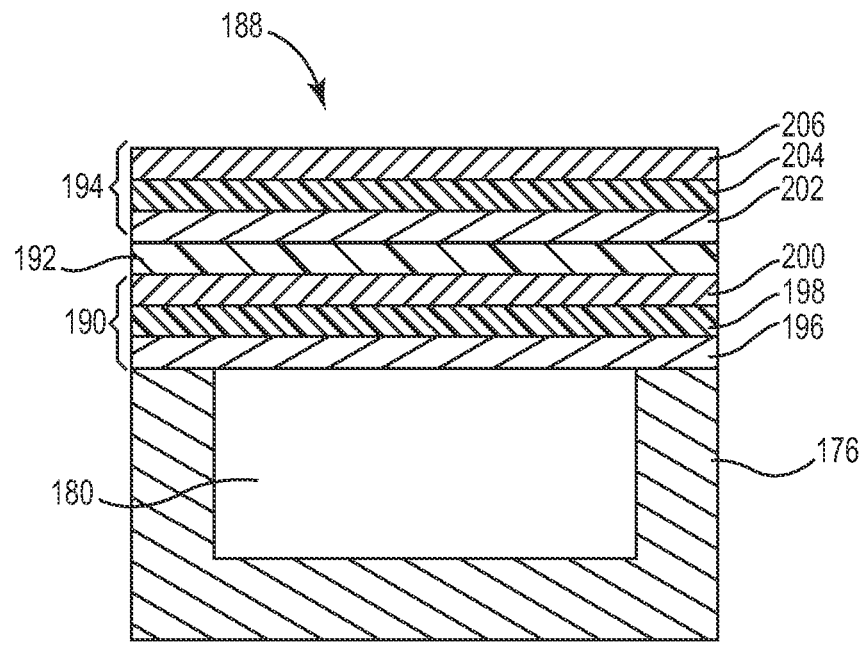
FIG. 13 is a schematic cross-sectional view of a power generator.

FIG. 13 is a schematic cross-sectional view of a power generator 188 in accordance with another illustrative embodiment of the power generation module 74 of FIG. 3. The power generator 188 can be provided as a component within an implantable device to generate power to meet at least some of the power requirements of the implantable device. The power generator 188 is similar in structure to the power generator 174 of FIG. 12, but includes a first flexible diaphragm 190, a second flexible diaphragm 194, and an intervening insulating layer 192.

Each of the first flexible diaphragm 190 and the second flexible diaphragm 194 include several layers. In the illustrated embodiment, the first flexible diaphragm 190 includes a first electrical conductor 196, a second electrical conductor 200, and a first piezoelectric layer 198 sandwiched or interposed between the first electrical conductor 196 and the second electrical conductor 200. Similarly, the second flexible diaphragm 194 includes a third electrical conductor 202, a fourth electrical conductor 206, and a second piezoelectric layer 204 sandwiched or interposed between the third electrical conductor 202 and the fourth electrical conductor 206.

When the first and second flexible diaphragms 190 and 194 flex or otherwise displace, and with reference to an arbitrary point in a cycle in which the first and second flexible diaphragms 190 and 194 flex back and forth in a cyclic manner, one of the flexible diaphragms is in tension while the other of the diaphragms is in compression. A time-dependent varying voltage differential can be captured within each of the first and second flexible diaphragms 190 and 194. Depending on which diaphragm is in compression and which is in tension, one of the flexible diaphragms will exhibit a positive electric field while the other exhibits a negative electric field. By placing an electrically insulating material (e.g., insulating layer 192) between the two flexible diaphragms 190, 194, each electric field can be captured rather than simply canceling each other out.

Figure 14:
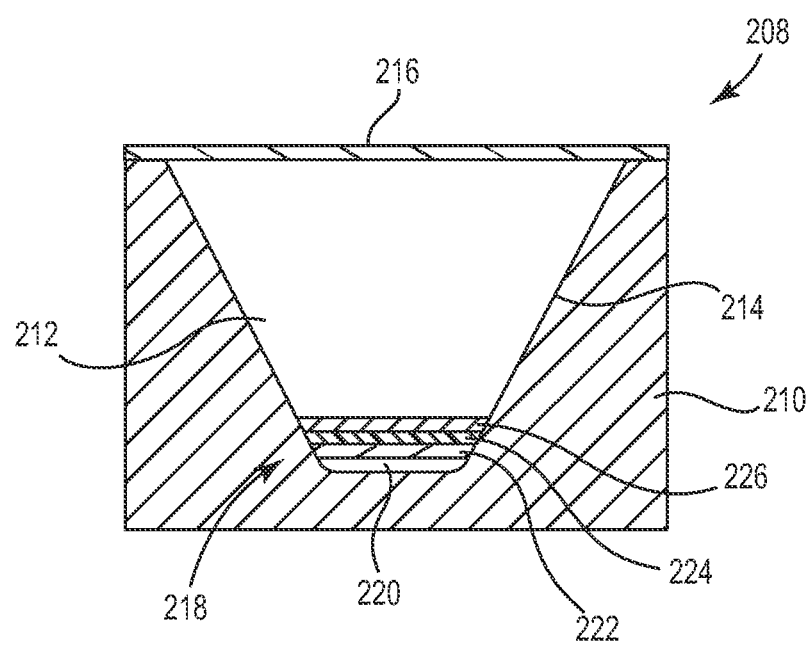
FIG. 14 is a schematic cross-sectional view of a pressure amplifier in accordance with an illustrative embodiment.

FIG. 14 is a schematic cross-sectional view of a pressure amplifier in accordance with an illustrative embodiment. In some embodiments, it may be useful to amplify the pressure fluctuations being sensed by an implantable sensor such as the implantable sensor 78 of FIG. 4. FIG. 14 provides an illustrative but non-limiting example of a pressure amplifier 208. The pressure amplifier 208 includes, as illustrated, a body 210 defining an interior cavity 212. The interior cavity 212 is defined at least in part by angled walls 214. A diaphragm 216 is disposed across an upper portion of the body 210, thereby enclosing and hermetically sealing the interior cavity 212. The diaphragm 216 is configured to be exposed, for example, to periodic pressure pulses within the body. In some embodiments, the pressure amplifier 208 will be disposed within an implantable medical device (e.g., the IMD 16 of FIG. 1) in such a way so as to be exposed to periodic pressure pulses exterior to the IMD 16. The interior cavity 212 is filled with a fluid such as an incompressible fluid for transmitting pressure through the interior cavity 212.

A power generating diaphragm 218 is disposed at a relative lower position within the interior cavity 212, leaving a small void 220 under the power generating diaphragm 198 so that the power generating diaphragm 218 is able to displace into the small void 200 in response to pressure pulses transmitted through the interior cavity 212 from the diaphragm 216. As can be seen in FIG. 14, the diaphragm 216 has a larger diameter (and thus a larger surface area) than a diameter of the power generating diaphragm 218.

The power generating diaphragm 218 includes a first electrical conductor 222, a second electrical conductor 226, and an intervening piezoelectric layer 224 that is sandwiched or interposed between the first electrical conductor 222 and the second electrical conductor 226. Movement of the diaphragm 216 is transmitted through the interior cavity 212 as pressure pulses and thus is transmitted to the power generating diaphragm 218. As the power generating diaphragm 218 displaces, a voltage differential forms between the first electrical conductor 222 and the second electrical conductor 226. This voltage differential can be converted into an electrical current for powering one or more components and/or to recharge a rechargeable power supply.

Due to the difference in the cross-sectional area of the diaphragm 216 relative to the power generating diaphragm 218, the pressure applied on the larger surface of diaphragm 216 is amplified onto the smaller surface of the power generating diaphragm 218 by a factor equal to the ratio of the areas of the two surfaces. Thus, the power generating diaphragm 218 will experience a greater pressure (or pressure difference) in comparison to the diaphragm 216. For example, if the diaphragm 216 and the power generating diaphragm 218 are both circular or substantially circular in shape and if the diaphragm 216 has a diameter twice that of the power generating diaphragm 218, there will be a four-fold pressure amplification.

Figure 15:
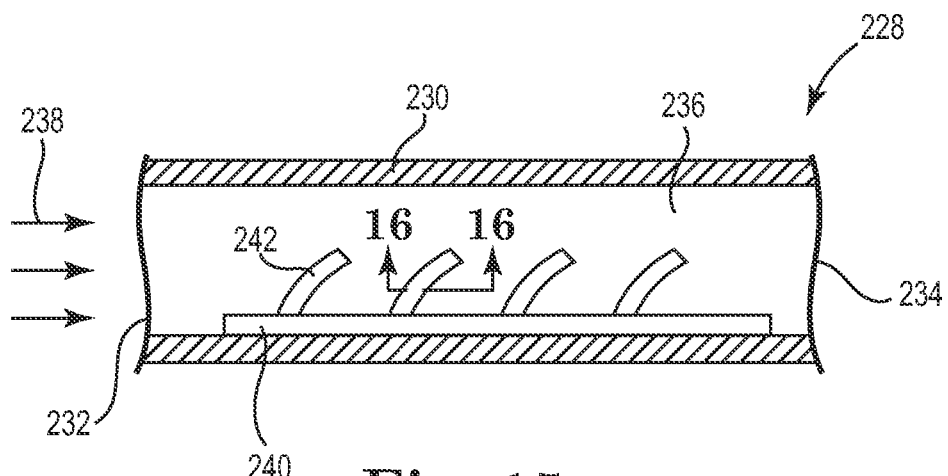
FIG. 15 is a schematic cross-sectional view of an implantable power generator.

FIG. 15 is a schematic cross-sectional view of a power generator 228 that is another illustrative but non-limiting example of the power generation module 68 of FIG. 3. The power generator 228 can, for example, be deployed within a patient's vasculature to generate power in response to the periodic pressure pulses caused by the beating of the heart. The power generator 228 includes a housing 230 that is configured to be deployed within the vasculature so that it is subjected to the aforementioned pressure pulses. The power generator 228 includes a first flexible diaphragm 232 that is disposed at an upstream end of the power generator 228, and a second flexible diaphragm 234 that is disposed at a downstream end of the power generator 228. The housing 230 defines an interior space 236 that is filled with a fluid in order to transmit pressure pulses through the interior space 236. The power generator 228 includes a base 240 and one or more piezoelectric assemblies 242 that are secured to the base 240.

Once the power generator 228 has been deployed, blood flow (indicated by the arrows 238) impinges on the first flexible diaphragm 232, causing the first flexible diaphragm 232 to flex inwards, thereby transmitting a pressure pulse through the housing 230 to the second flexible diaphragm 234. As a result, the second flexible diaphragm 234 flexes outwardly, as illustrated. As a pressure pulse is transmitted through the interior space 236 via the fluid therein, the one or more piezoelectric assemblies 242 can flex or bend in response to the pressure pulse.

Figure 16:
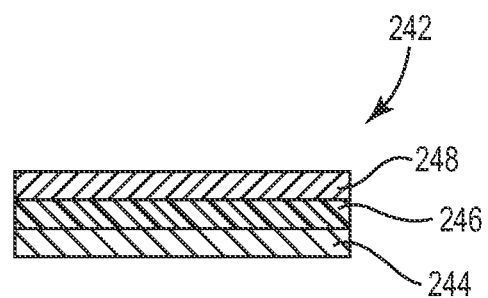
FIG. 16 is a cross-sectional view of a piezoelectric assembly taken along line 16-16 in FIG. 15.

As seen in FIG. 16, which is a cross-section of a piezoelectric assembly 242 taken along line 16-16 of FIG. 15, each piezoelectric assembly 242 includes a first electrical conductor 244, a second electrical conductor 248, and a piezoelectric layer 246 sandwiched or interposed between the first electrical conductor 244 and the second electrical conductor 248. As the piezoelectric assembly 242 flexes, a voltage differential is formed between the first electrical conductor 244 and the second electrical conductor 248. This voltage differential can be converted into an electrical current for powering one or more components and/or to recharge a rechargeable power supply. In some embodiments, the base 240 can include appropriate circuitry such as the power circuitry 76 of FIG. 3.

Figure 17:
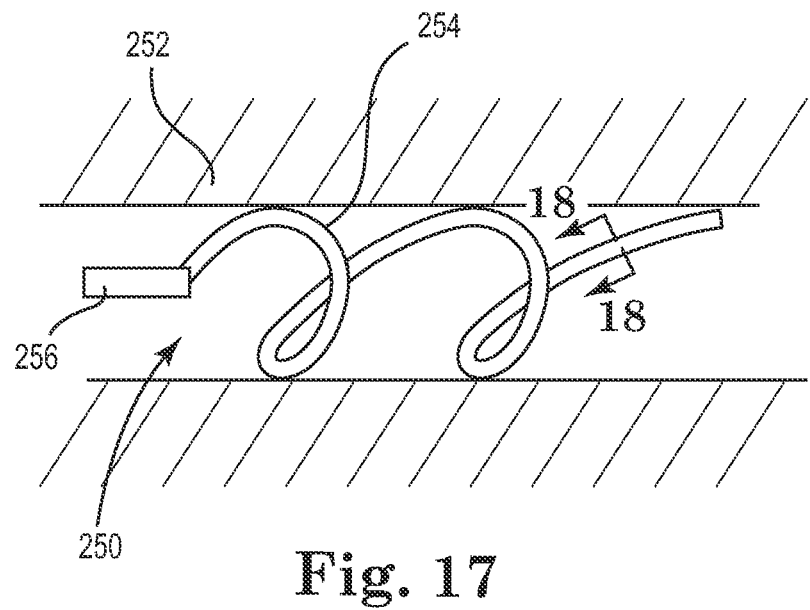
FIG. 17 is a schematic illustration of a piezoelectric power generator.

FIG. 17 is a schematic cross-sectional view of an implantable power generator including a piezoelectric anchoring member that, in addition to anchoring an implantable medical device within the vasculature, is also used to provide at least some of the power requirements of the implantable medical device. As shown in FIG. 17, a piezoelectric power generating structure 250 is disposed within a patient's vasculature 252.

The piezoelectric power generating structure 250 includes a helical anchor 254 that is attached to an implantable device 256 such as, for example, an implantable pressure sensor. In some embodiments, the helical anchor 254 may represent at least a portion of the anchor assembly 58 of FIG. 2 or the anchor assembly 84 of FIG. 4. The helical anchor 254 may also be part of other anchoring assemblies, or in some embodiments may itself be the anchor assembly.

Figure 18:
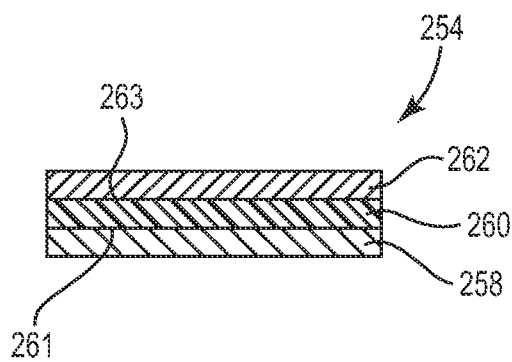
FIG. 18 is a cross-sectional view of a portion of the piezoelectric power generator of FIG. 17.

FIG. 18 is a cross-sectional view of the helical anchor 254, taken along line 18-18 of FIG. 17. As further shown in FIG. 18, and in some embodiments, the helical anchor 254 has a composite ribbon structure that includes a first electrical conductor 258, a second electrical conductor 262 and a piezoelectric layer 260 that is sandwiched or interposed between the first electrical conductor 258 and the second electrical conductor 262. The piezoelectric layer 260 has a first surface 261 and a second surface 263. In some embodiments, the first electrical conductor 258 is in contact with the first surface 261 and the second electrical conductor 262 is in contact with the second surface 263.

In some embodiments, physiologic activities such as pulsitile pressure forces, movement caused by respiration, movement caused by skeletal muscle and the like can apply a physiologic force to the helical anchor 254. In some embodiments, blood flow can apply a physiologic force to the helical anchor 254. As blood flows through the vasculature 252, the resulting pressure pulses can cause the vasculature 252 to flex and bend, and in some cases also expand and contract. The pressure pulses likewise cause the helical anchor 254 to bend and flex. As the helical anchor 254 flexes or otherwise moves in response to the physiologic forces, a time-dependent voltage differential is generated between the first electrical conductor 258 and the second electrical conductor 262. As with other embodiments discussed herein, this voltage differential can be converted into an electrical current that can be used for powering at least some of the components within an implantable medical device and/or to recharge a rechargeable power supply.

In the illustrated embodiment, the piezoelectric power generating structure 250 is disposed within the vasculature 252. In some embodiments, it is contemplated that the helical anchor 254 could instead be disposed about an exterior of the vasculature 252 and thus could be used to generate power to at least partially power a device (such as implantable device 256) that is deployed in a location that is outside the vasculature 252. For example, the vasculature 252 can be an artery or a vein, and the helical anchor 254 can be wrapped around an exterior of the artery or vein. The implantable device 256 can be coupled to the helical anchor 254 but can be disposed anywhere within the body that is exterior to the artery or vein. The implantable device 256 can be located next to the helical anchor 254, or the implantable device 256 can be located some distance away. The helical anchor 254 is electrically coupled to the implantable device 256 to permit power generated by the anchor 254 to be transmitted to the implantable device 256.

Figure 19:
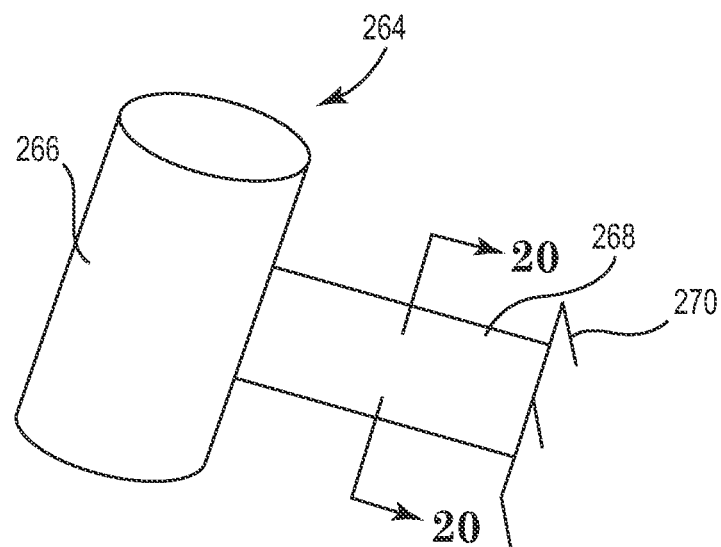
FIG. 19 is a schematic cross-sectional view of an implantable power generator.
Figure 20:
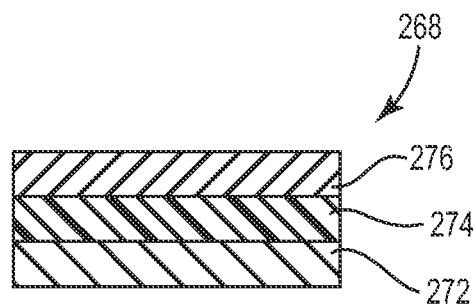
FIG. 20 is a cross-sectional view of a portion of the implantable power generator of FIG. 19.

FIGS. 19 and 20 provide another illustrative example of a piezoelectric power generator 264 that is configured to be implanted within a patient at a location that subjects the piezoelectric power generator 264 to periodic movement. Examples of periodic movement include breathing and the movement caused by a beating heart. Another example includes skeletal muscles and the body movement that can be generated via the skeletal muscles. In some embodiments, the movement may be generated by a change in temperature occurring within the body. The piezoelectric power generator 264 includes an implantable device 266, such as an implantable sensor, an implantable therapeutic device, or the like. A piezoelectric bridge 268 extends from the implantable device 266 to an anchor 270. The anchor 270 is configured to be secured to an internal structure within the patient, such as a bone, a muscle, heart tissue, a blood vessel, and the like. In some embodiments, the anchor 270 is sutured to one of the aforementioned internal structures. For example, when implanted within a chamber of the heart, the anchor 270 may be sutured to the myocardial tissue to tether the implanted device 266 within the chamber.

FIG. 20 is a cross-sectional view of the piezoelectric bridge 268, taken along line 20-20 of FIG. 19. As can be further seen in FIG. 20, the piezoelectric bridge 268 has a composite structure that includes a first electrical conductor 272, a second electrical conductor 276, and a piezoelectric layer 274 that is sandwiched or interposed between the first electrical conductor 272 and the second electrical conductor 276. It will be appreciated that as the implantable device 266 moves in response to an applied bodily force, the piezoelectric bridge 268 will bend and flex, thereby operating as a moment arm.

As the piezoelectric bridge 268 flexes or otherwise moves in response to periodic pressure pulses, the piezoelectric layer 274 produces an electric field that causes a time-dependent voltage differential to form between the first electrical conductor 272 and the second electrical conductor 276. As with other embodiments discussed herein, this voltage differential can be converted into an electrical current for powering one or more components within the implantable device 266 and/or recharge a rechargeable power supply.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device, comprising:
   a housing including an internal cavity;
   a flexible anchor assembly coupled to the housing and configured to secure the implantable medical device within a body lumen, the flexible anchor assembly comprising a helical structure including:
   a helical piezoelectric layer having a first surface and an opposing second surface;
   a first electrically conductive layer disposed in contact with the first surface of the helical piezoelectric layer;
   a second electrically conductive layer disposed in contact with the second surface of the helical piezoelectric layer, the helical piezoelectric layer configured to displace in response to periodic diameter fluctuations of the body lumen and generate a voltage differential between the first and second electrically conductive layers; and
   power circuitry configured to convert the voltage differential between the first and second electrically conductive layers into an operating current for powering one or more components of the implantable medical device.

2. The implantable medical device of claim 1, further comprising a sensor module disposed within the interior cavity of the housing, the sensor module configured to sense one or more physiologic parameters within the body lumen.

3. The implantable medical device of claim 1, further comprising a wireless communication module disposed within the internal cavity.

4. The implantable medical device of claim 1, further comprising a rechargeable power supply disposed within the internal cavity.

* * * * *